(12) United States Patent
Oshima et al.

(10) Patent No.: US 7,326,150 B2
(45) Date of Patent: Feb. 5, 2008

(54) FAT COMBUSTION VALUE CALCULATING METHOD, FAT COMBUSTION VALUE CALCULATING DEVICE, AND EXERCISE MACHINE

(75) Inventors: Yoshitake Oshima, Kyoto (JP); Toshikazu Shiga, Kyoto (JP)

(73) Assignee: Omron Healthcare Co., Ltd., Tokyo (JP)

( * ) Notice: Subject to any disclaimer, the term of this patent is extended or adjusted under 35 U.S.C. 154(b) by 1002 days.

(21) Appl. No.: 10/181,043

(22) PCT Filed: Jan. 17, 2001

(86) PCT No.: PCT/JP01/00255

§ 371 (c)(1),
(2), (4) Date: Jul. 12, 2002

(87) PCT Pub. No.: WO01/52738

PCT Pub. Date: Jul. 26, 2001

(65) Prior Publication Data

US 2003/0013995 A1    Jan. 16, 2003

(30) Foreign Application Priority Data

Jan. 18, 2000 (JP) .............................. 2000-008494

(51) Int. Cl.
*A63B 21/00* (2006.01)
*A63B 22/00* (2006.01)

(52) U.S. Cl. ........................... 482/1; 600/300; 600/531

(58) Field of Classification Search ................ 482/1–9, 482/900–902; 600/300, 301, 519, 531, 532
See application file for complete search history.

(56) References Cited

U.S. PATENT DOCUMENTS 5,297,558 A * 3/1994 Acorn et al. ................ 600/532

(Continued)

FOREIGN PATENT DOCUMENTS

EP    1 059 102 A1    12/2000

(Continued)

OTHER PUBLICATIONS

Wasserman et al., "Exercise Physiology in Health and Disease" American Review of Respiratory Disease, vol. 112, 1975.

(Continued)

*Primary Examiner*—Glenn Richman
(74) *Attorney, Agent, or Firm*—Morrison & Foerster LLP

(57) ABSTRACT

In the fat burning value calculating apparatus (6), an electrocardiographic signal is detected (1, 41, 45-47) at the start of exercise, and a heart rate is calculated from the detected value. Further, a power of heart rate variability is calculated, and an AT level is determined from the variability power. Once the AT level is determined, a preset exercise program is executed. A work load during the exercise is detected, and consumed calories are calculated. Thereafter, the electrocardiographic signal during the exercise is detected, the heart rate is calculated from the detected signal, and a fat burning rate during the exercise is calculated. A fat burning amount is calculated from the consumed calories and the fat burning rate, their accumulated values are also calculated, and these values are displayed. As a result, it is possible to provide a fat burning value calculating method and a fat burning value calculating apparatus (6) which ensure accurate calculation of the fat burning rate and the fat burning amount of an individual during exercise, regardless of increase/decrease of exercise intensity.

14 Claims, 15 Drawing Sheets

U.S. PATENT DOCUMENTS

| | | | |
|---|---|---|---|
| 6,104,947 A * | 8/2000 | Heikkila et al. | 600/519 |
| 6,387,053 B1 * | 5/2002 | Pessenhofer | 600/531 |
| 6,554,776 B1 * | 4/2003 | Snow et al. | 600/532 |

FOREIGN PATENT DOCUMENTS

| | | |
|---|---|---|
| JP | 6331760 | 12/1994 |
| JP | 7016230 | 1/1995 |
| JP | 07084994 | 3/1995 |
| JP | 08038462 | 2/1996 |
| JP | 9173500 | 7/1997 |
| JP | 9294727 | 11/1997 |
| JP | 11056827 | 3/1999 |
| WO | WO99/43392 | 9/1999 |

OTHER PUBLICATIONS

Ikegami, "Accommodation of Body Function", 1997.

* cited by examiner

PROGRAM a

PROGRAM b

PROGRAM c

FAT COMBUSTION VALUE CALCULATING METHOD, FAT COMBUSTION VALUE CALCULATING DEVICE, AND EXERCISE MACHINE

TECHNICAL FIELD

The present invention relates to a fat burning value calculating method, a fat burning value calculating apparatus and an exercise machine which calculate fat burning rate, fat burning amount and others based on a physiological signal measured from a living body engaged in exercise.

BACKGROUND ART

Conventional apparatuses for calculating a fat burning amount (fat consumption amount) are disclosed in Japanese Patent Laying-Open No. 9-173500: "Training System", Japanese Patent Laying-Open No. 7-84994: "Calculation Device for Consumed Fat Amount", and Japanese Patent Laying-Open No. 6-331760: "Fat Consumption Measuring Equipment".

In the training system of Japanese Patent Laying-Open No. 9-173500, a respiratory metabolism measuring device is used to experimentally calculate a fat burning rate for each of dozens of test subjects, and a fat burning ratio (%) is estimated from the results, using a statistic technique, in response to an elapsed time from the start of exercise.

With the consumed fat amount calculation device of Japanese Patent Laying-Open No. 7-84994, a fat consumption rate (%) is calculated in accordance with a table prepared based on the characteristics of the fat burning rate that it is in proportion to the exercise time and in reverse proportion to the exercise intensity.

With the fat consumption measuring equipment of Japanese Patent Laying-Open No. 6-331760, a fat consumption amount is calculated based on a fat consumption rate that is obtained from the exercise time and the oxygen amount necessary for exercise.

These conventional methods for calculating the fat burning amount, however, pose the following problems.

In Japanese Patent Laying-Open No. 9-173500, the fat burning rate is calculated based solely on the elapsed time from the start of exercise; it does not take account of a change of the fat burning rate due to a change of the exercise intensity. Thus, if an exercise intensity is increased/decreased during the exercise, an appropriate fat burning rate may not be applied, which would deteriorate accuracy in calculation of the fat burning amount.

In Japanese Patent Laying-Open No. 7-84994, the fat burning rate is calculated using the table prepared with the fat burning amount in reverse proportion to the exercise intensity. This again does not conform to the relation between the exercise intensity and the fat burning rate, or the characteristics that carbohydrate and fat burning rates are around 50% when the exercise intensity is up to 50-60% of the maximum exercise intensity and, when the exercise intensity exceeds the relevant range, the fat burning rate decreases along with an increase of the work load, and the fat burning rate becomes 0% with the exercise of the maximum work load. Thus, an error occurs in calculation of the fat burning amount.

International Patent Publication No. WO99/43392 discloses a method for controlling a load of an exercise machine employing an anaerobic threshold (AT), wherein the anaerobic threshold (AT) work load is obtained from characteristics of heart rate variability or the like. The publication, however, only discloses how the AT as an exercise level is obtained; it does not disclose how the AT is specifically utilized.

Herein, the heart rate variability is calculated by first detecting an electrocardiographic signal with an electrocardiographic sensor, calculating a heart rate from a detected peak value of the electrocardiographic signal, and utilizing a prescribed formula, the detail of which will be described later.

The present invention has been made taking notice of the conventional problems as described above, and its object is to provide a fat burning value calculating method, a fat burning value calculating apparatus and an exercise machine which can accurately calculate a fat burning rate and a fat burning amount of a person during exercise regardless of increase/decrease of the exercise intensity.

DISCLOSURE OF THE INVENTION

The fat burning value calculating apparatus according to the present invention is provided with physiological signal measuring means for measuring a physiological signal from a living body during exercise, and fat burning rate calculating means for calculating a fat burning rate based on the physiological signal obtained by the physiological signal measuring means. The physiological signal includes at least a heart rate obtained by an electrocardiographic signal or a pulse wave signal, and heart rate variability obtained by the electrocardiographic signal or the pulse wave signal.

In the present invention, the physiological signal including the heart rate obtained by the electrocardiographic signal or the pulse wave signal from the living body during exercise and the heart rate variability obtained by the electrocardiographic signal or the pulse wave signal is measured, and the fat burning rate is calculated based on the physiological signal obtained.

Since the fat burning rate is calculated from the physiological signal during exercise that changes at times throughout the exercise, the fat burning rate can be calculated more accurately than in the case of the conventional techniques (including the one taking no account of the change of the fat burning rate, and the one using a table prepared such that the fat burning amount is in reverse proportion to the exercise intensity). Accordingly, it is possible to provide accurate and valid information to a person who exercises with an aim to burn the fat.

Herein, the "physiological signal" is a concept incorporating the "electrocardiographic signal" and the "pulse wave signal". The "heart rate" is a concept incorporating a "heart rate" and a "pulse rate". The "heart rate interval" is a concept incorporating a "heart rate interval" and a "pulse rate interval", and the "variability of heart rate intervals" is a concept incorporating "variability of heart rate intervals" and "variability of pulse rate intervals".

In another aspect of the present invention, the fat burning value calculating apparatus is provided with physiological signal measuring means for measuring a physiological signal from a living body during exercise, anaerobic threshold determining means for determining an anaerobic threshold (AT) from the physiological signal obtained by the physiological signal measuring means, and fat burning rate calculating means for calculating a fat burning rate based on an exercise intensity at the determined anaerobic threshold. Specifically, the fat burning rate is calculated, for example, from a ratio between the exercise intensity at the anaerobic threshold and an exercise intensity at a time of the exercise.

Herein, the exercise intensity at the anaerobic threshold may be determined in any of the following manners:

(1) to determine from a change of a power value of variability of heart rate intervals that is obtained from an electrocardiographic signal or a pulse wave signal;

(2) to determine from a change of entropy of the variability of heart rate intervals that is obtained from the electrocardiographic signal or the pulse wave signal;

(3) to determine from a change of a power value of heart rate variation spectrum;

(4) to determine from a change of a product of a heart rate and a blood pressure under vasoconstriction;

(5) to determine using a previously measured anaerobic threshold; or (6) to determine by breathing gas analysis from, e.g., an inflection point of an increase of carbon dioxide emission with respect to an increase of oxygen intake.

Although the calculating method described above is for calculating the fat burning rate, a fat burning amount can also be calculated accurately using the fat burning rate calculated and consumed calories calculated from the exercise intensity.

In the case where the apparatus is further provided with input means for inputting a fat burning amount as a target, and remaining time calculating means for calculating a remaining time required to reach the target fat burning amount from the fat burning amount calculated by the fat burning amount calculating means and an exercise time, it is possible to let a person find out how long he/she needs to continue the exercise to achieve the desired fat burning amount, which gives him/her an incentive and pleasure to work out.

Alternatively, in the case where accumulated value calculating means for calculating an accumulated value of the fat burning amount from the start of the exercise is provided, he/she can find out how much fat has been burnt. This also enhances his/her motivation to exercise.

The exercise machine of the present invention is provided with an exercise load device causing a test subject to do a prescribed load exercise, an exercise load device control unit controlling the exercise load device, physiological signal measuring means for measuring a physiological signal of the test subject at a time of the exercise, anaerobic threshold determining means, calculating heart rate variability from the physiological signal measured by the physiological signal measuring means, for determining an anaerobic threshold (AT) based on the heart rate variability, fat burning rate calculating means, storing an exercise intensity at the anaerobic threshold determined by the anaerobic threshold determining means, for calculating a fat burning rate from a relation between an exercise intensity at a time of the exercise and the stored exercise intensity at the anaerobic threshold, and display means for displaying information about fat burnt based on the fat burning rate calculated by the fat burning rate calculating means.

This exercise machine incorporates the fat burning value calculating apparatus employing the AT. The "information about fat burnt" displayed by the display means includes a fat burning amount, a fat burning amount accumulated during the exercise, a time required to reach a target fat burning amount and others.

BEST MODES FOR CARRYING OUT THE INVENTION

Hereinafter, embodiments of the present invention will be described with reference to the drawings.

Figure 1:
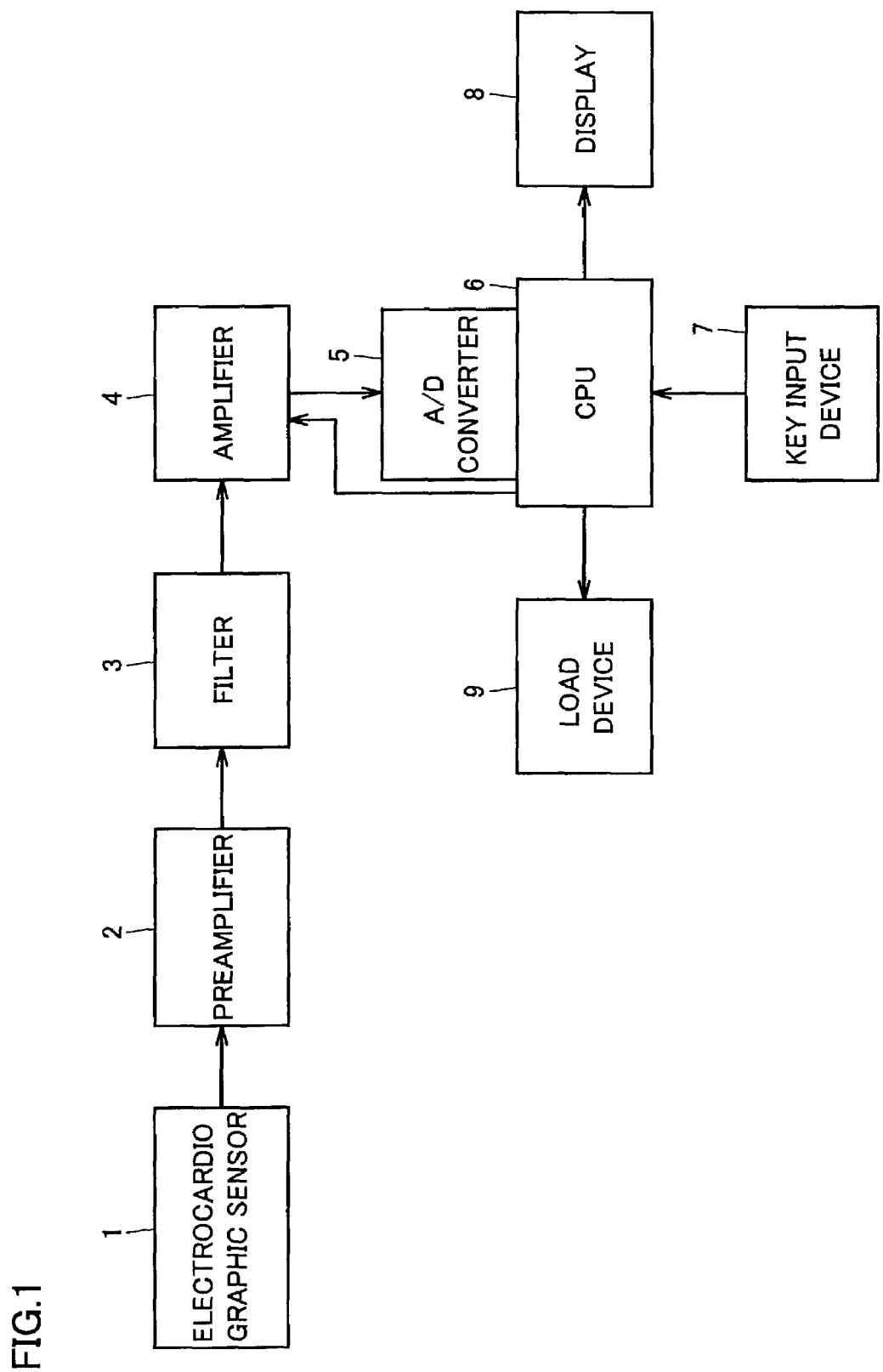
FIG. 1 is a block diagram showing a circuit configuration of a bicycle ergometer as an example of the exercise machine incorporating the fat burning value calculating apparatus of the present invention.

FIG. 1 is a block diagram showing a circuit configuration of a bicycle ergometer as an example of the exercise machine incorporating the fat burning value calculating apparatus of the present invention. The ergometer includes an electrocardiographic sensor 1 detecting an electrocardiographic signal, a preamplifier 2 amplifying the output signal, a filter 3 removing noise, an amplifier 4 further amplifying the electrocardiographic signal to an appropriate level, an A/D converter 5, a CPU 6 performing various kinds of processing, a key input device 7, a display 8 displaying a work load value, a fat burning amount and others, and a load device 9 having a variable rotation load.

CPU 6 has various functions which include: a function to control load device 9 by determining, based on a physiological signal from a living body under a work load, an appropriate work load from a pattern in variation of the physiological signal during the exercise; a function to calculate a fat burning rate based on the work load thus determined; a function to calculate a fat burning amount from the fat burning rate thus calculated and consumed calories calculated from the work load and the exercise time measured; and a function to calculate accumulated values of the consumed calories, the fat burning amount and others.

Figure 2:
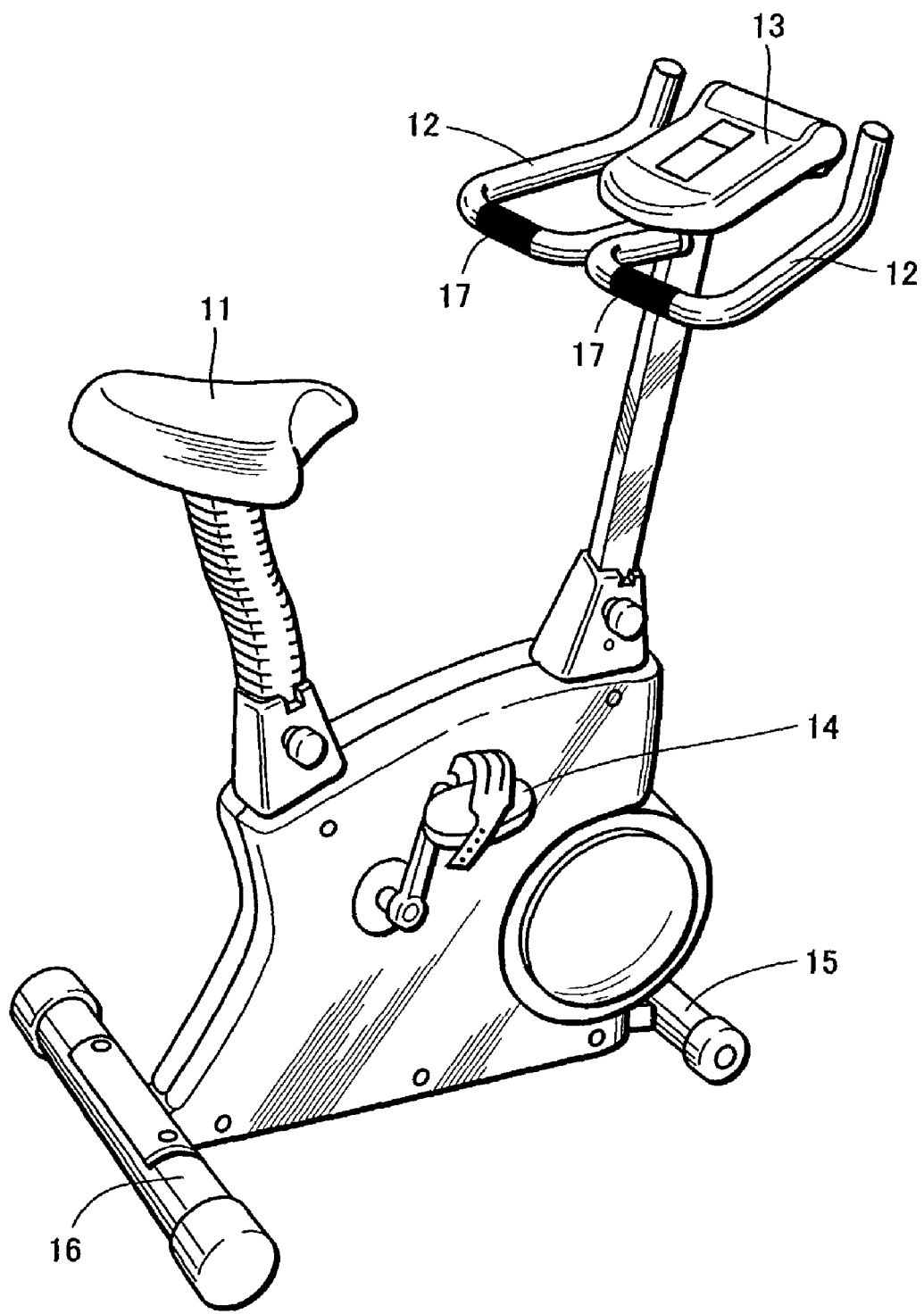
FIG. 2 is a perspective view of the bicycle ergometer.

FIG. 2 is a perspective view of the bicycle ergometer. Referring to FIG. 2, the ergometer includes a saddle 11, handles 12, a manipulation unit 13 having key input device 7, display 8 and an alarm (not shown), pedals 14, a front foot frame 15, and a hind foot frame 16. Handles 12 are provided with a pair of electrodes (physiological signal measuring means) 17 for electrocardiographic detection. When an exercising person grips the portions of handles 12 corresponding to electrodes 17 with respective hands during exercise, the hands come into contact with electrodes 17, and the electrocardiographic signal is detected from the hands.

With this ergometer, a test subject (an exercising person) sits on saddle 11 and works on pedals 14 to rotate them for exercise. A load is applied to pedals 14 to give them weight corresponding to the degree of the work load. For the greater load, the larger amount of exercise is naturally needed to rotate pedals 14 a fixed number of times, as is well known.

Figure 3:
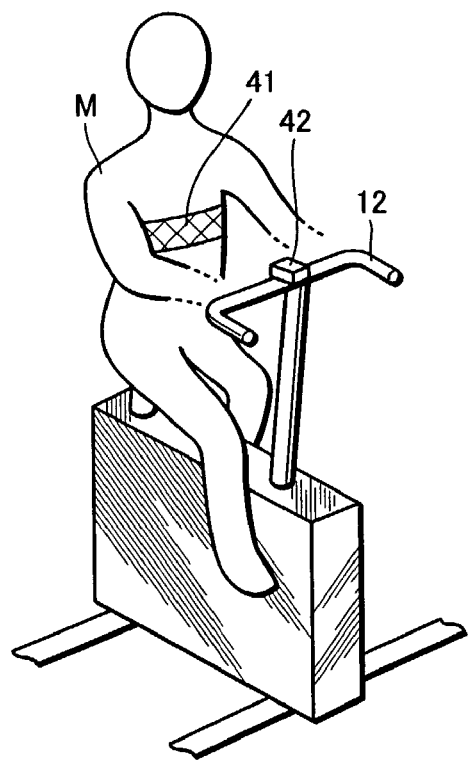
FIG. 3 shows a state where an alternative electrocardiographic sensor for use with the bicycle ergometer is attached to an exercising person.

Although electrodes 17 for electrocardiographic detection are provided in handles 12 in the embodiment of FIG. 2, various modifications are possible. For example, in FIG. 3, a chest belt 41 provided with a pair of electrodes and a transmitter is worn around the chest of a subject M, and a receiver 42 (corresponding to manipulation unit 13 in FIG. 2) is provided in handle 12. In this case, the electrocardiographic signal detected from the chest of subject M is transmitted by radio to receiver 42 for processing.

Figure 4:
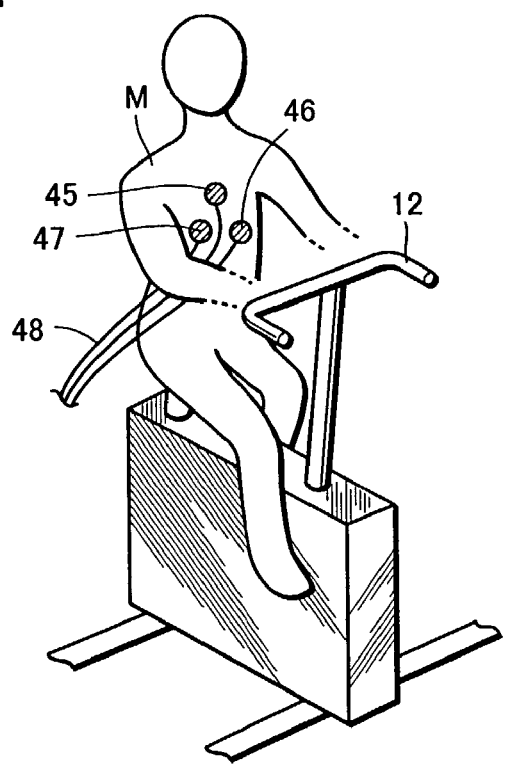
FIG. 4 shows a state where yet another example of the electrocardiographic sensor used with the bicycle ergometer is attached to an exercising person.

An embodiment shown in FIG. 4 is of a chest leads type which has three electrodes 45, 46 and 47 of + (plus), − (minus) and G (ground), respectively, attached to the chest of subject M and also connected by wire 48 to the circuitry within the ergometer body for detection of the electrocardiographic signal.

Figure 5:
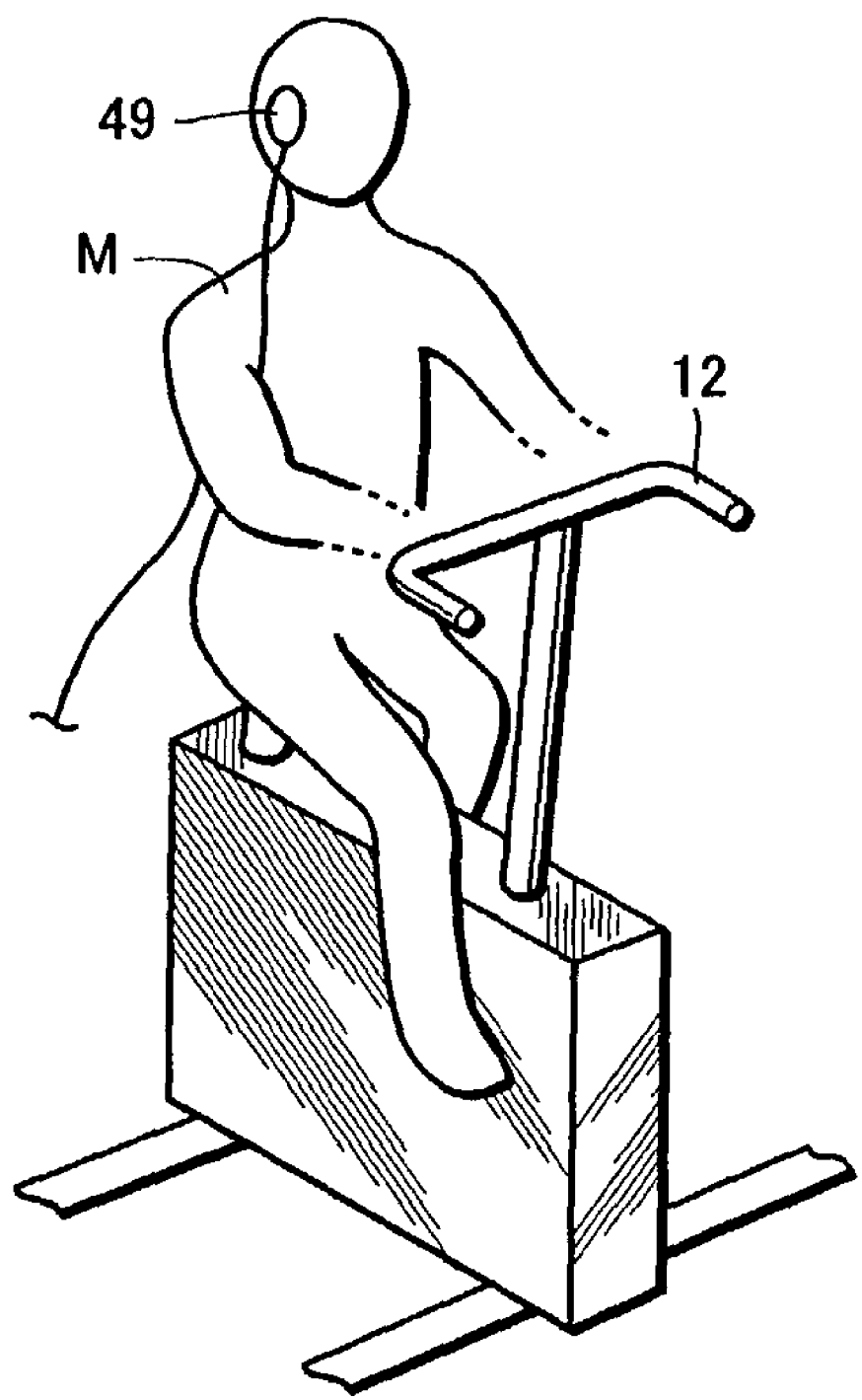
FIG. 5 shows a state where a pulse wave sensor used with the bicycle ergometer is attached to an exercising person.

In an embodiment shown in FIG. 5, a pulse wave sensor 49, instead of the electrocardiographic sensor, is attached to an earlobe of the subject M for detection of a pulse wave signal, and data concerning variability of pulse rate, pulse rate intervals and others (variability value, entropy, power value and others) are extracted. An anaerobic threshold (AT) as will be described later may be obtained based on such data about the variability of pulse rate and pulse rate intervals.

In the exercise machines configured as described above, an appropriate work load value is determined, based on a physiological signal with respect to a change of work load, such as an electrocardiographic signal detected by an electrocardiographic sensor or a pulse wave signal detected by a pulse wave sensor, from the pattern in variation of the relevant physiological signal under the work load. The work load for rotating pedals 14 is then changed corresponding to the determined work load.

The waveform of the heart rate signal detected by the electrocardiographic sensor has peaks that can be clearly recognized, so that it is easy to grasp their intervals. Although it may be possible to grasp pulse rate intervals from the waveform of the pulse wave detected by the pulse wave sensor, the waveform from the pulse wave sensor may include unclear peaks. Thus, from the standpoint of reliability, it is preferable to detect the heart rate signal.

Now, referring to the flow charts in FIGS. 6 and 7, the method for determining an anaerobic threshold (AT) from a change of the physiological signal like the electrocardiographic signal or the pulse wave signal, and calculating a fat burning rate and a fat burning amount based on a work load (hereinafter, referred to as "AT work load") at the determined anaerobic threshold is specifically described.

Figure 6:
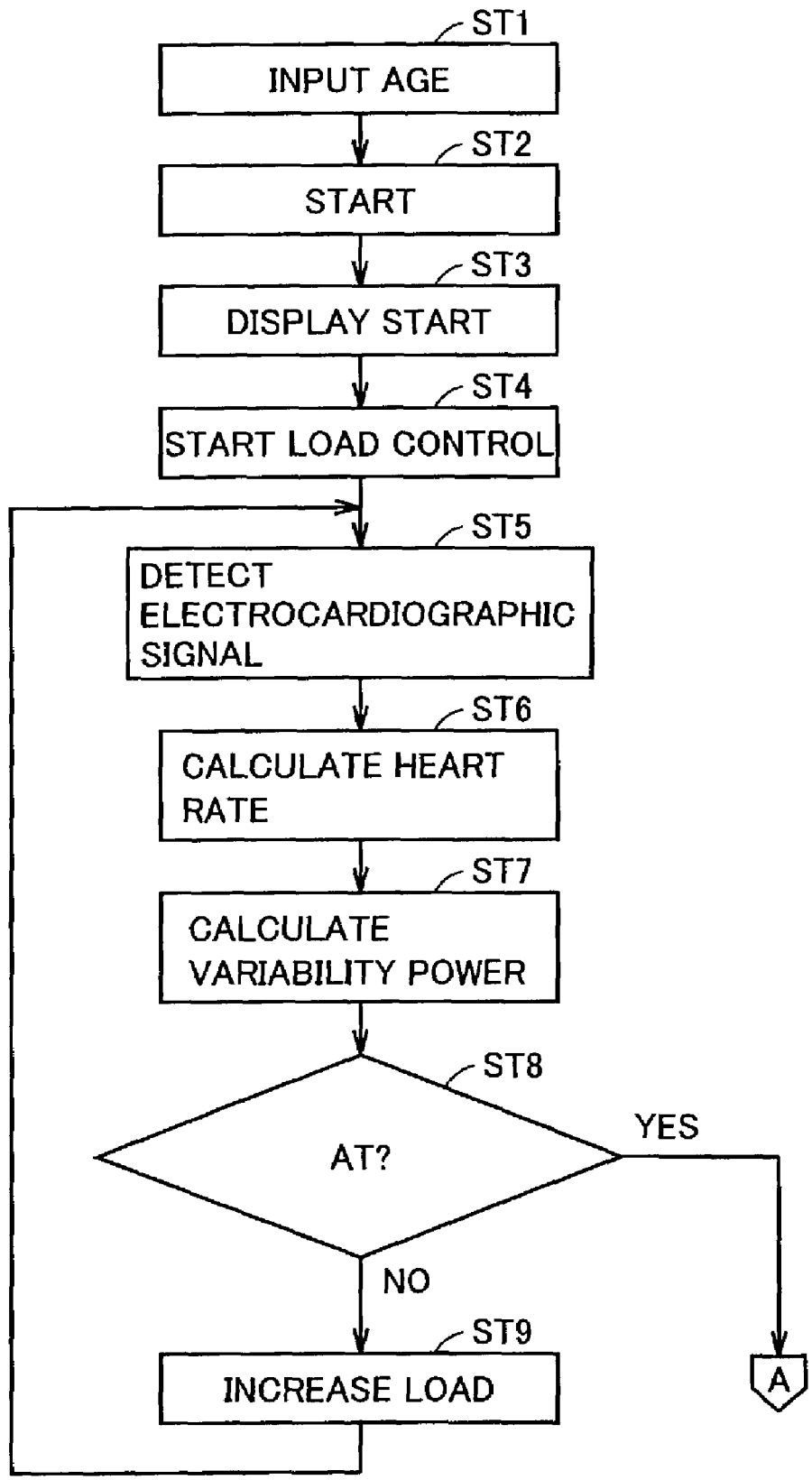
FIG. 6 is a flow chart specifically showing an example of the process of determining the anaerobic threshold (AT) from a change of a physiological signal and calculating a fat burning rate and a fat burning amount based on a work load (AT work load) at the determined anaerobic threshold.
Figure 7:
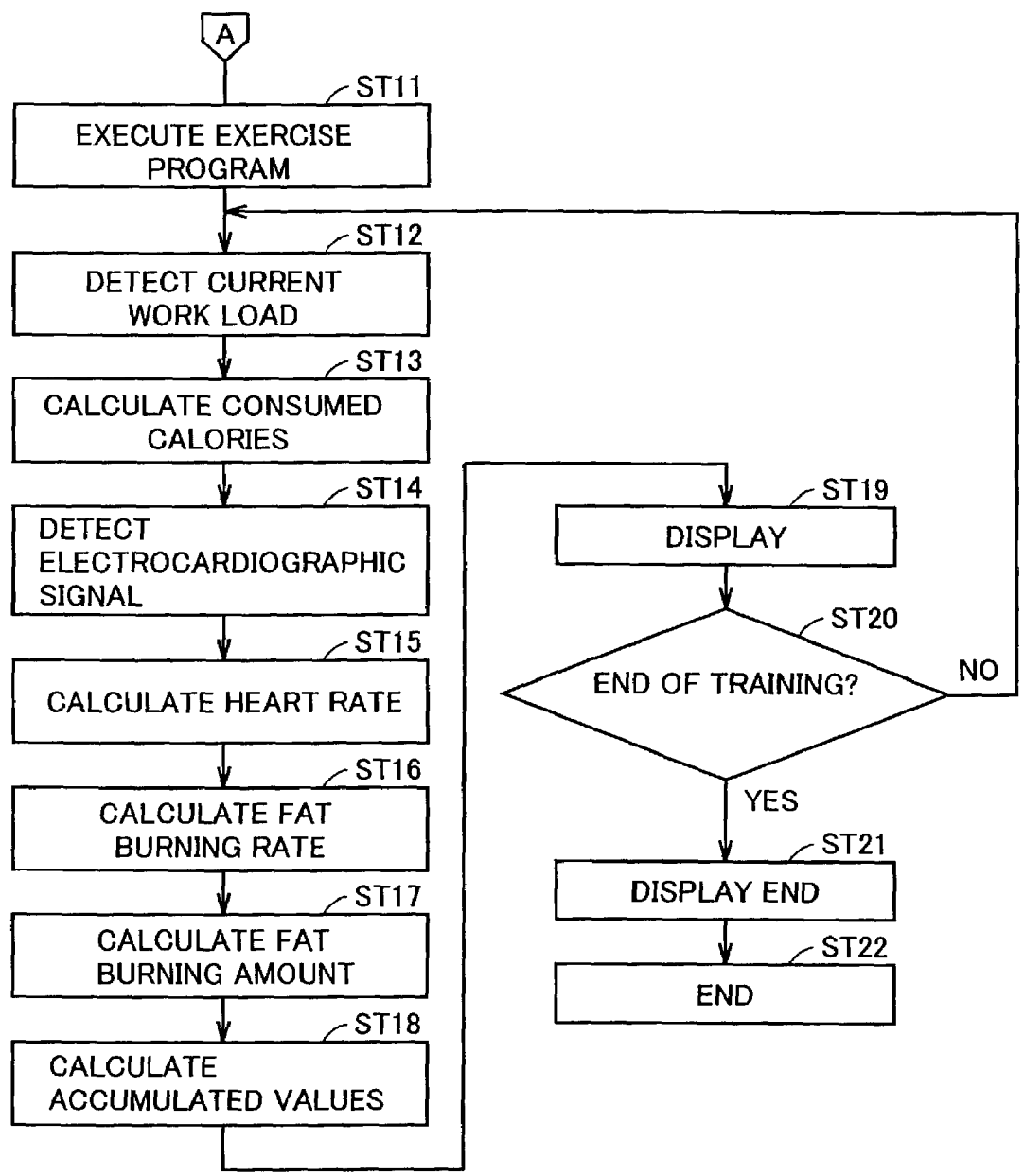
FIG. 7 is a flow chart continued from FIG. 6.

The flow charts in FIGS. 6 and 7 show an example of the process of calculating a power value of heart rate variability, determining an AT work load from a convergence level of the power value of heart rate variability, and then calculating a fat burning amount. To determine the AT work load, the power value of pulse rate variability as described above or the like may be employed instead of the power value of heart rate variability.

Firstly, in step (hereinafter, abbreviated to "ST") 1, the age is input via key input device 7 shown in FIG. 1. When a training start key is depressed (ST2), "start training" is displayed on display 8 (ST3), and control of load device 9 is started (ST4). For example, two-minute warming up at an initial work load of 20 [W] is followed by application of a ramp load of 15 [W] per minute. Next, an electrocardiographic signal is detected by electrocardiographic sensor 1 (ST5), a heart rate is calculated from detected peak values of the electrocardiographic signal (ST6), and a power value of heart rate variability is calculated according to the following expression (1) (ST7).

$$\text{Power}(n)[ms^2] = \{RR(n) - RR(n-1)\}^2 \quad (1)$$

This Power (n) obtained as the square of a difference between the current cycle and the previous cycle is called a power value of the heart rate variability. An average value of this power value for 30 seconds is calculated at an interval of 15 seconds, for example, which is used to obtain variation characteristics of the power with respect to an increase of the work load.

When the power value becomes lower than a predetermined bottom value and when a difference from the power value of the previous cycle calculated by the following expression (2) becomes lower than a predetermined reference value, it is determined that a convergence point has been reached, and the AT work load is determined (ST8).

$$\Delta\text{power} = \text{power}(n-1) - \text{power}(n) \quad (2)$$

Figure 8A:
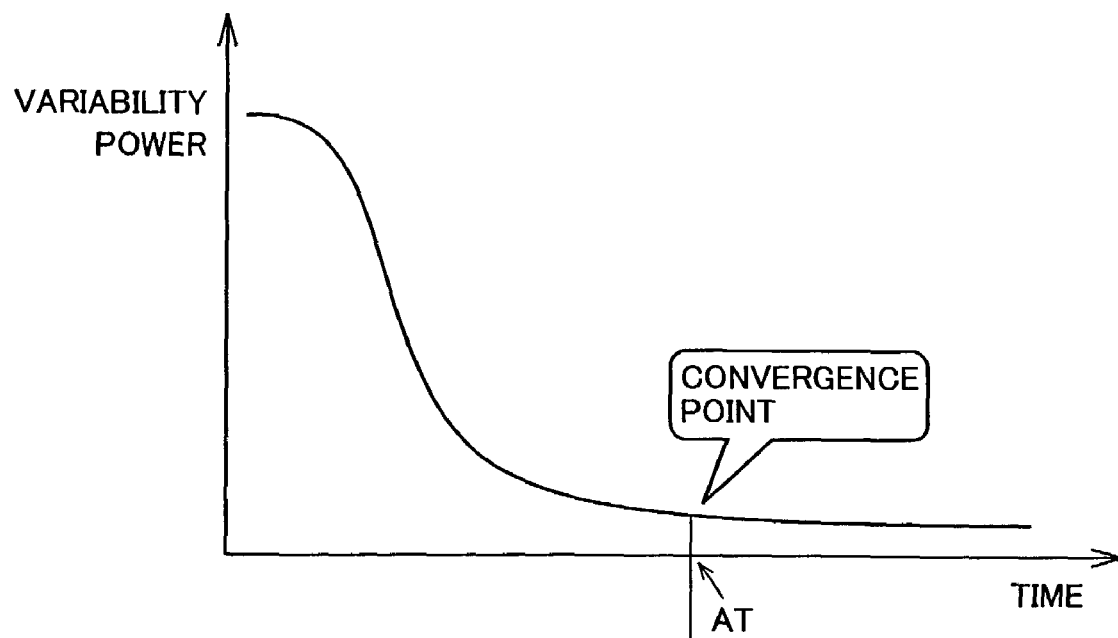
FIG. 8A shows a relation between time and power of heart rate variability.
Figure 8B:
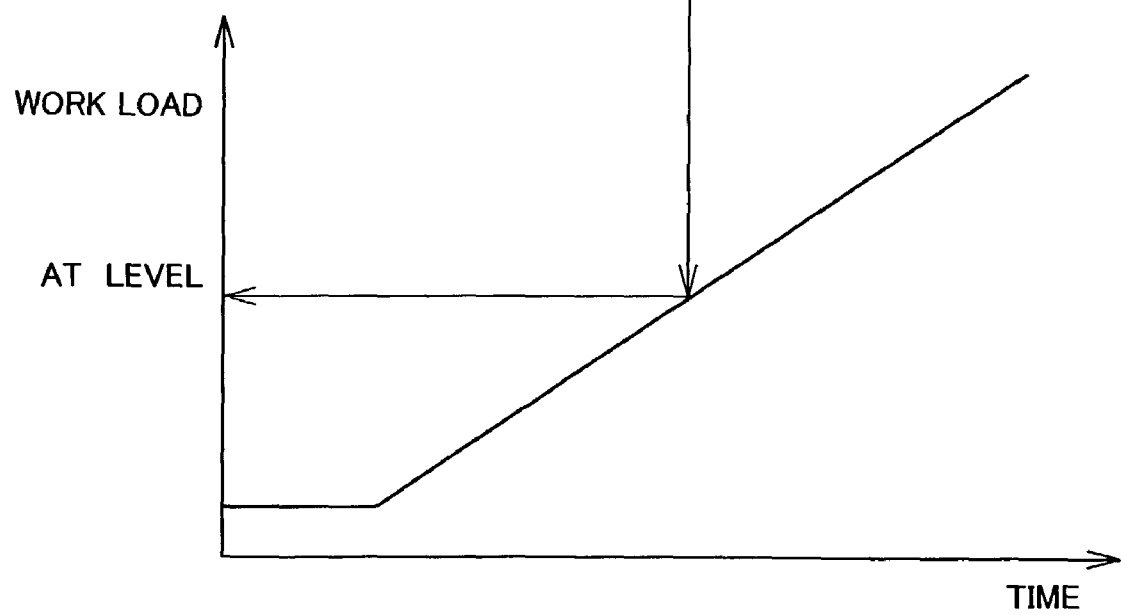
FIG. 8B shows a relation between time and work load in the exercise machine.

FIGS. 8A and 8B illustrate a relation between the power value and the load. The power value changes as shown in FIG. 8A, from which a convergence point is detected. A work load at that time is then obtained, as shown in FIG. 8B.

Figure 10A:
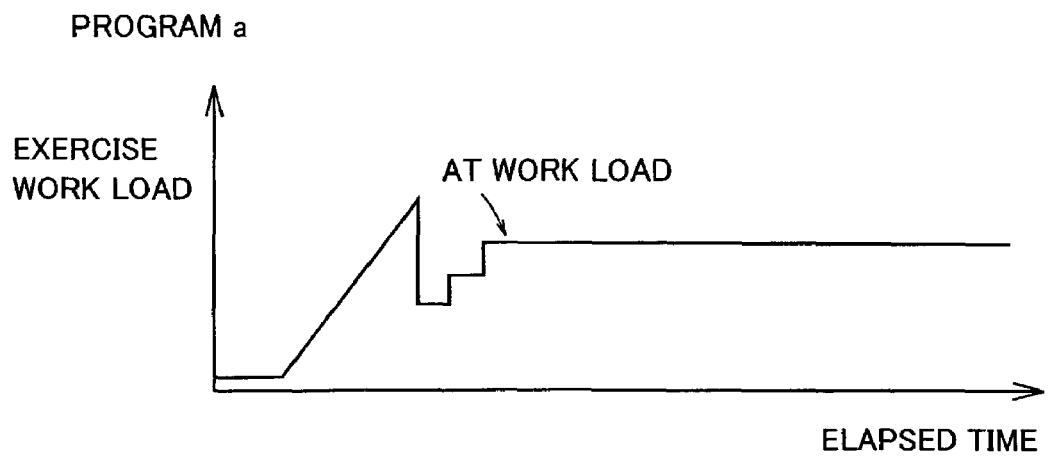
FIGS. 10A-10C show various exercise programs for control of the work load preset based on the AT work load.
Figure 10B:
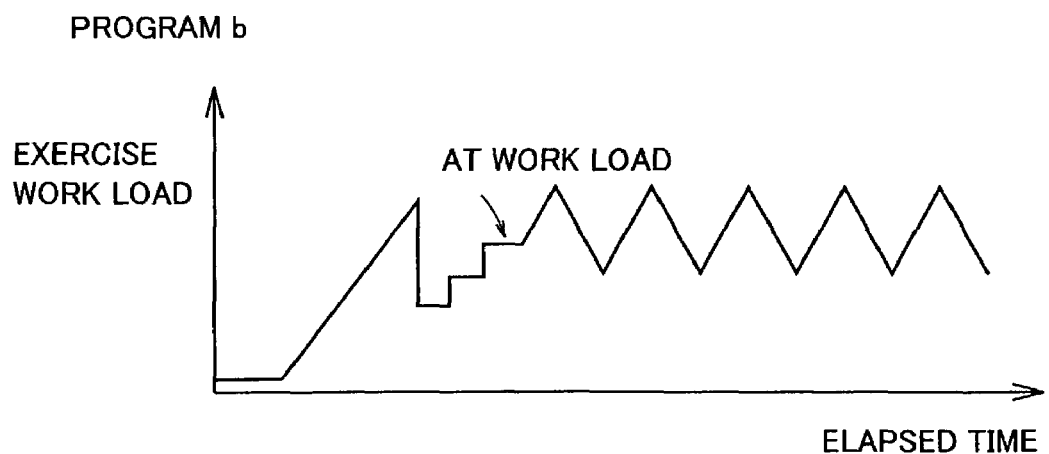
Figure 10C:
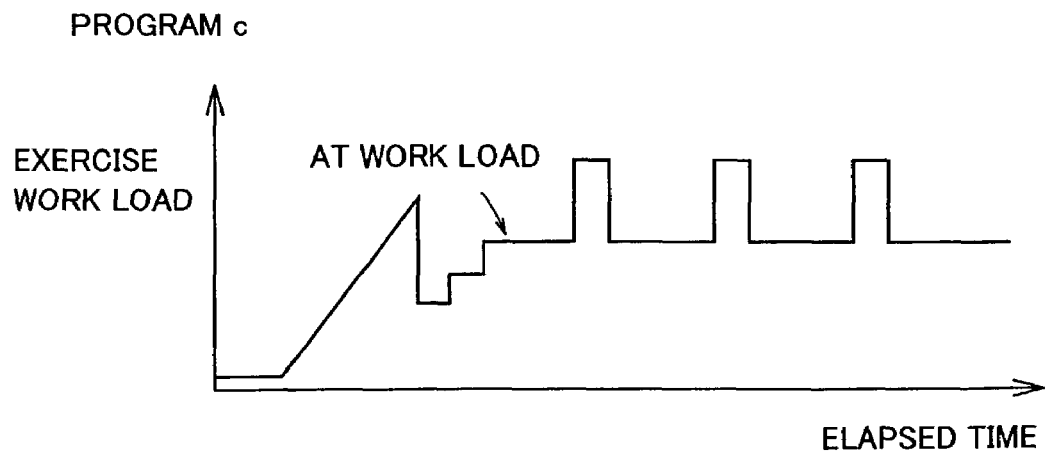

If it is not determined as the AT work load, the decision in ST8 is NO. With the work load gradually increased (ST9), the steps ST5-ST8 are repeated. When it is determined as the AT work load, the process goes to various exercise programs performing control of the work load preset based on the AT work load, as shown in FIGS. 10A-10C (ST11).

Next, a current work load during the exercise controlled by the exercise program is detected (ST12), and consumed calories per unit time during the exercise are calculated according to the following expression (3) (ST13).

$$\text{Consumed calories [kcal/min]} = \text{work load[Watt] during exercise} \div 0.232 \times 14.3 \div 1000 \quad (3)$$

where
Watt: displayed work load,
0.232: exercise efficiency of ergometer (23.2%),
14.3: 1W=14.3 cal/min,
÷1000: cal is converted to kcal.

The electrocardiographic signal during the exercise is detected (ST14), a heart rate is calculated from the detected signal (ST15), and a fat burning rate during the exercise is calculated (ST16).

Figure 11:
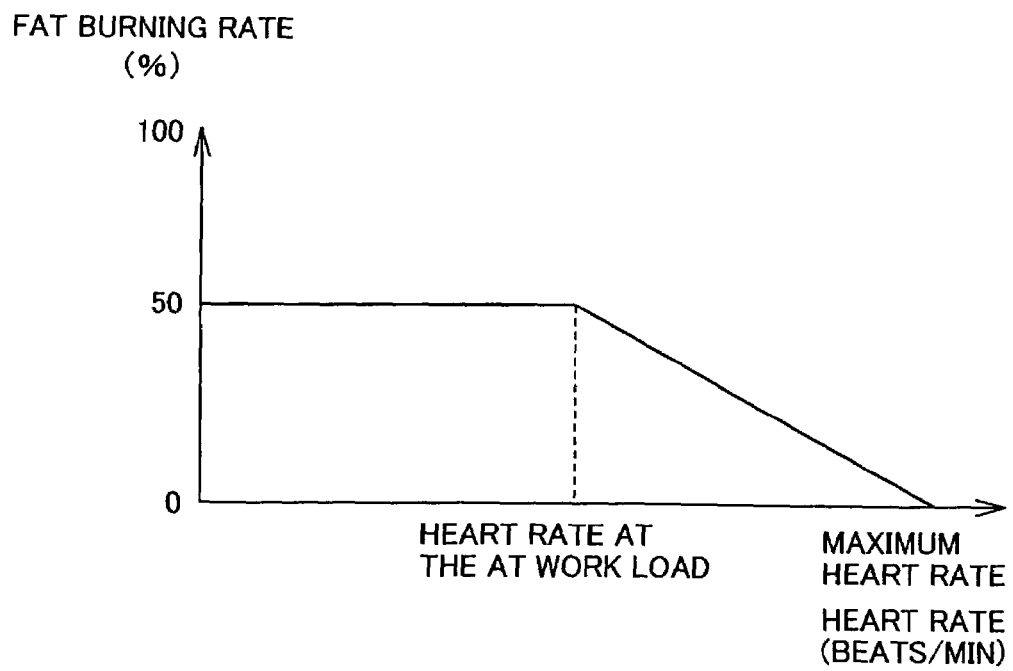
FIG. 11 shows a relation between the heart rate and the fat burning rate.

FIG. 11 shows a relation between the fat burning rate and the heart rate. Referring to FIG. 11, although the fat burning rate changes in accordance with the heart rate, when the heart rate during the exercise is not greater than the heart rate at the AT work load (hereinafter, referred to as "AT heart rate"), the fat burning rate is constant at 50% regardless of the heart rate. When the heart rate becomes greater than the AT heart rate, the fat burning rate decreases in reverse proportion to the increase of the heart rate, and the fat burning rate at the maximum heart rate (220−age) becomes 0%.

Thus, when the heart rate is greater than the AT heart rate, the fat burning rate is calculated by the following expression (4).

$$\text{Fat burning rate}[\%] = -\{50/(\text{maximum heart rate} - \text{AT heart rate})\} \times \text{heart rate during exercise} + \{50/(\text{maximum heart rate} - \text{AT heart rate})\} \times \text{maximum heart rate} \quad (4)$$

Based on the fat burning rate calculated from the expression (4) and the consumed calories, a fat burning amount per unit time is calculated from the following expression (5) (ST17).

$$\text{Fat burning amount }[g/\min] = \text{consumed calories }[\text{kcal}/\min] \times \text{fat burning rate }[\%] \div 9 \quad (5)$$

Here, the product of the consumed calories and the fat burning rate is divided by 9 because 9 kcal is necessary to burn 1 g of fat.

Further, the exercise time is measured, and accumulated values of the consumed calories and the fat burning amount are calculated from the exercise time, the consumed calories per unit time and the fat burning amount per unit time (ST18). These values are displayed on display 8 (ST19).

Figure 12:
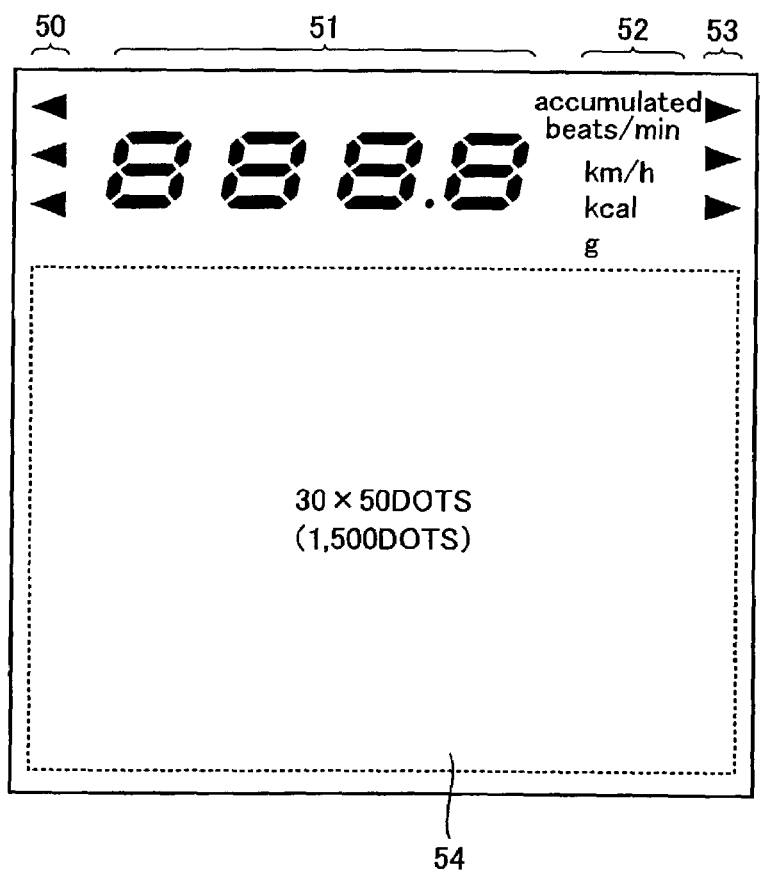
FIG. 12 is a top plan view showing a specific example of the display unit of the display shown in the block diagram of FIG. 1.

The consumed calories, the fat burning amount and others are displayed on a display unit of display 8 as shown in FIG. 12. The display unit is formed of an LCD, and has a program display mark region 50, a data display region 51, a unit display region 52 and a program display mark region 53 at the upper portion, and has a graphic display region 54 at the lower portion.

Figure 13A:
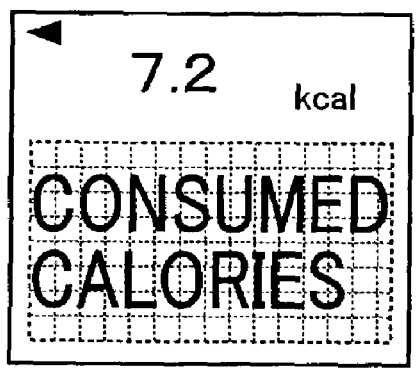
FIGS. 13A-13D are top plan views showing specific examples of various displays on the display unit shown in FIG. 12.
Figure 13B:
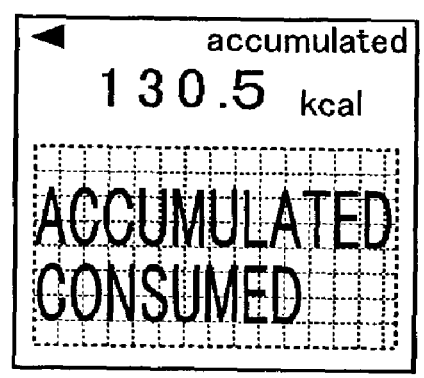
Figure 13C:
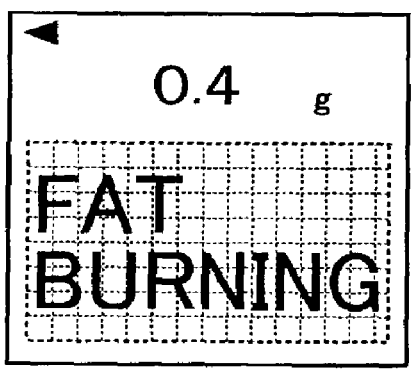
Figure 13D:
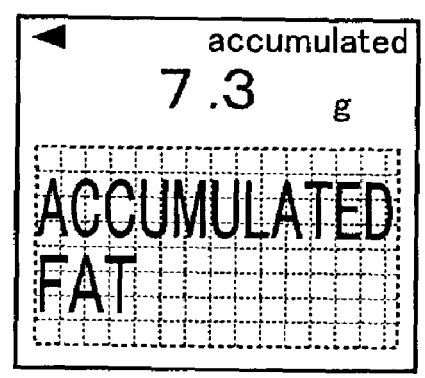

Specific display examples on this display unit are shown in FIGS. 13A-13D. FIGS. 13A, 13B show the case where the consumed calories and the accumulated consumed calories are displayed, and FIGS. 13C, 13D show the case where the fat burning amount and the accumulated fat burning amount are displayed. In either case, a numerical value of the consumed calories, the fat burning amount or the like is displayed on data display region 51 at the upper portion, and characters such as "CONSUMED CALORIES", "FAT BURNING AMOUNT" or the like are displayed and scrolled on graphic display region 54 at the lower portion.

Thereafter, when a training end key on key input device 7 of FIG. 1 is depressed (ST20), "end training" is displayed on display 8 (ST21), and the program is terminated (ST22). When the training end key is not depressed, the exercise program is continued, and the steps ST12-ST20 are repeated.

Figure 14:
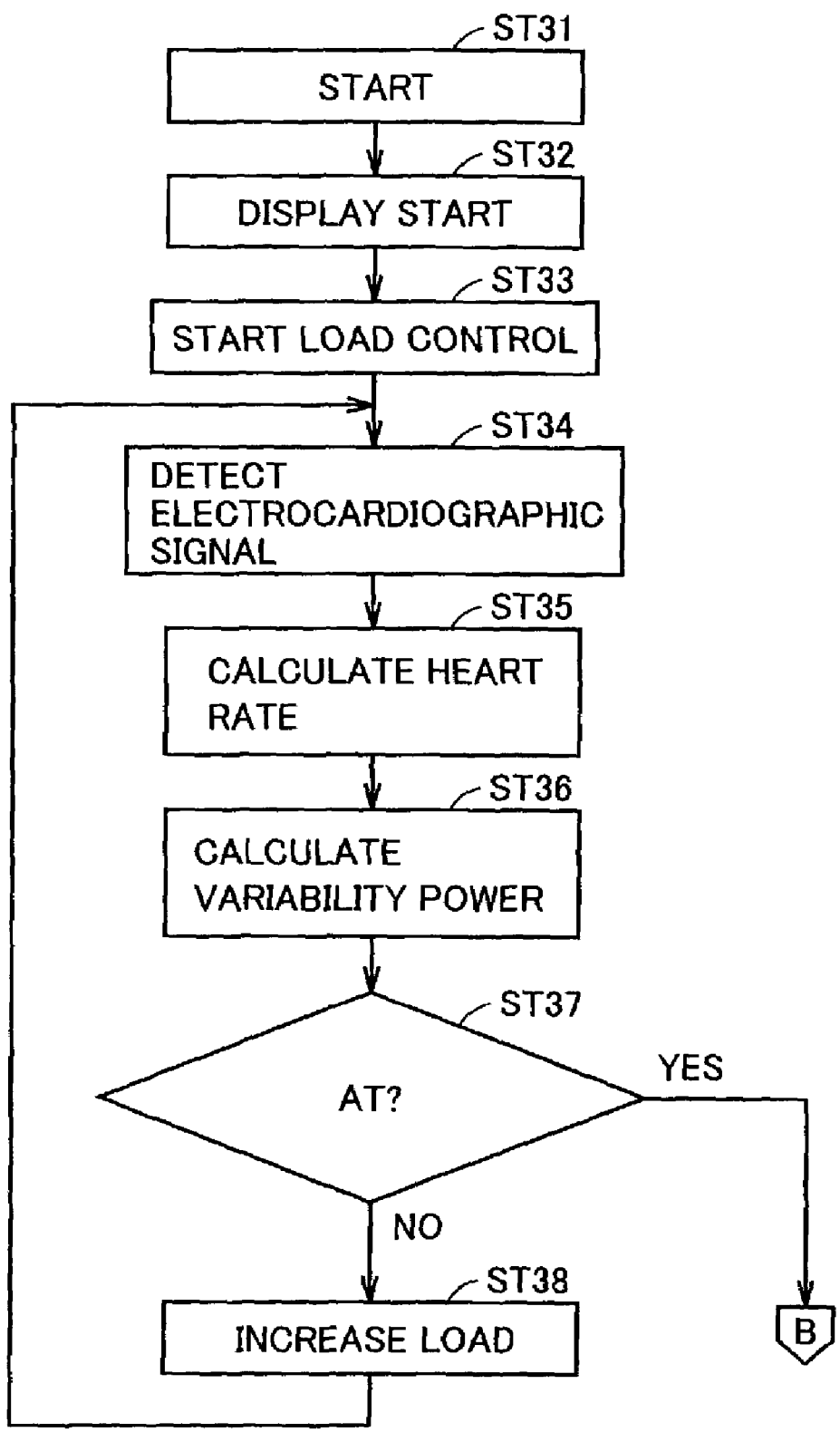
FIG. 14 is a flow chart specifically illustrating an example of the process of calculating the fat burning rate and the fat burning amount from the ratio between the work load at a time of the exercise and the AT work load.
Figure 15:
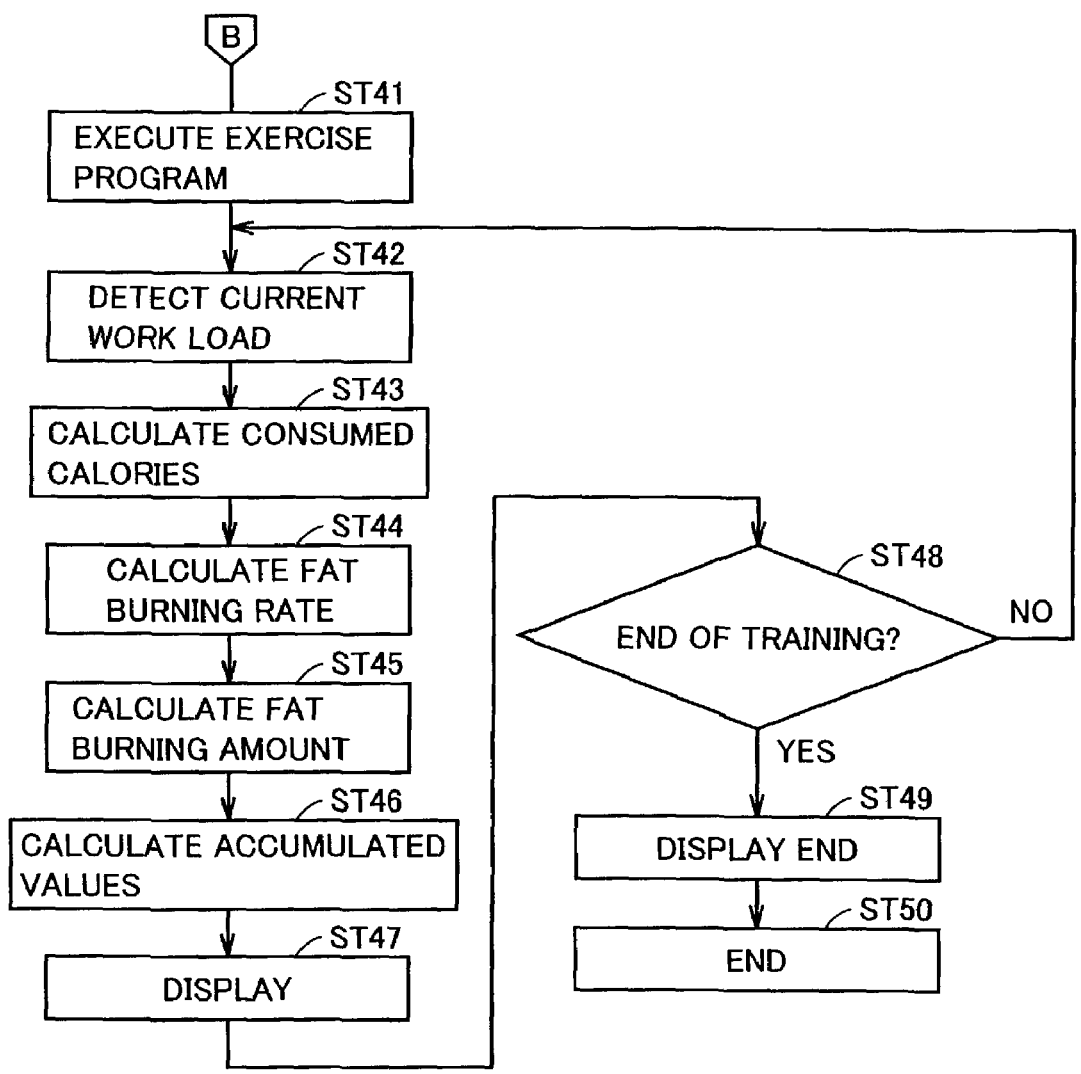
FIG. 15 is a flow chart continued from FIG. 14.

Although the fat burning rate was calculated from the ratio between the heart rate during the exercise and the AT heart rate in the flow charts shown in FIGS. 6 and 7, the fat burning rate may be calculated from a ratio between the work load during the exercise and the AT work load, as shown in the flow charts of FIGS. 14 and 15.

Figure 9A:
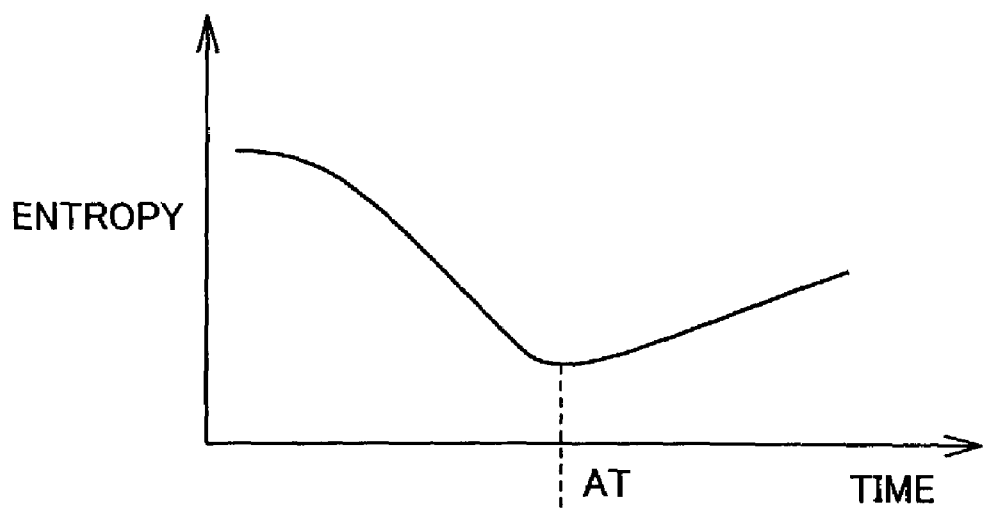
FIG. 9A shows an entropy change of heart rate variability.
Figure 9B:
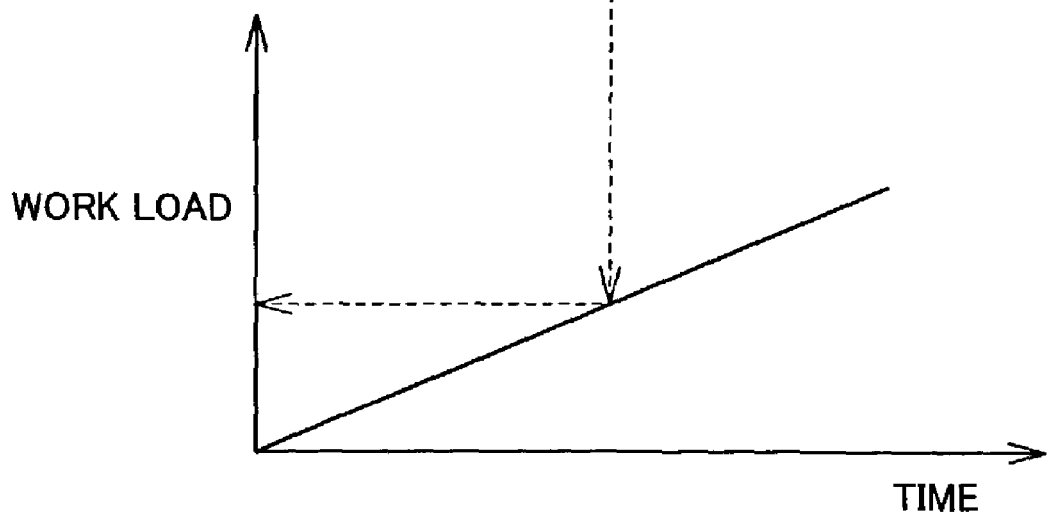
FIG. 9B shows a gradual increase of the work load over time in the exercise machine.

More specifically, in the flow charts shown in FIGS. 14 and 15, when the training start key on key input device 7 in FIG. 1 is first depressed (ST31), "start training" is displayed on display 8 (ST32), and control of load device 9 is started (ST33). An electrocardiographic signal is detected by electrocardiographic sensor 1 (ST34), the heart rate is calculated from the peak values of the electrocardiographic signal (ST35), and the power is calculated according to the expression (1) above (ST36). The characteristic change of this power is used to determine convergence, and the AT work load is determined (ST37). When it is not determined as the AT work load, the decision in ST37 is NO. The work load is gradually increased (ST38), and the steps ST34-ST37 are repeated. When it is determined as the AT work load, the process goes to various exercise programs performing control of the work load preset based on the AT work load as shown in FIGS. 9A and 9B (ST41).

Next, a current work load during the exercise controlled by the exercise program is detected (ST42), and consumed calories per unit time during the exercise are obtained from the expression (3) above (ST43). A fat burning rate is then obtained in the following manner (ST44).

Figure 17:
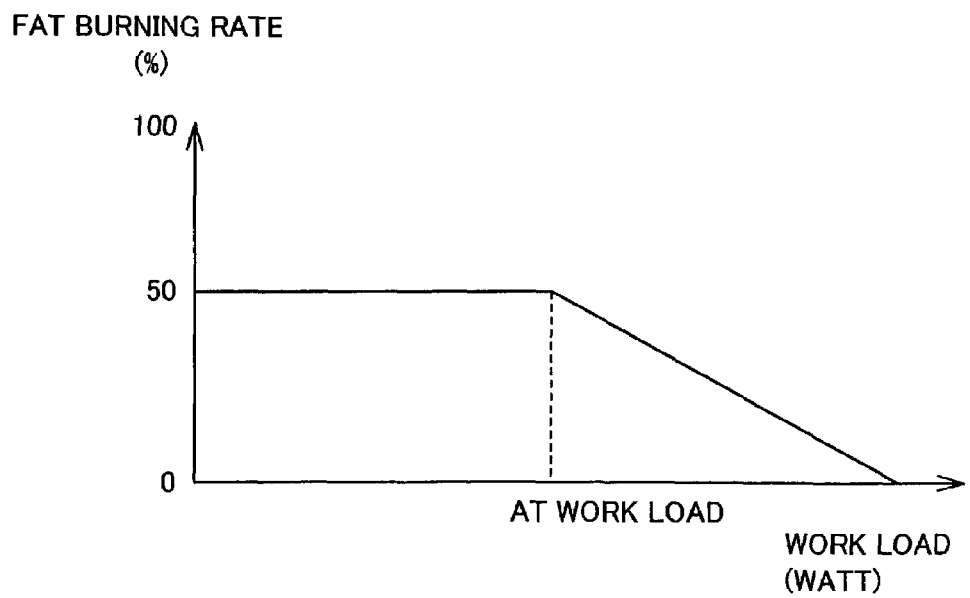
FIG. 17 shows a relation between the work load and the fat burning rate.

As shown in FIG. 17, the fat burning rate with the work load not greater than the AT work load is constant at 50%. By comparison, when the work load becomes greater than the AT work load, the fat burning rate decreases in reverse proportion to the increase of the work load, and it becomes 0% at the maximum work load.

Therefore, the fat burning rate when the work load is greater than the AT work load is calculated by the following expression (6).

$$\text{Fat burning rate}(>AT)\,[\%] = -\{50/(\text{maximum work load} - \text{AT work load})\} \times \text{work load during exercise} + \{50/(\text{maximum work load} - \text{AT work load})\} \times \text{maximum work load} \quad (6)$$

Figure 16:
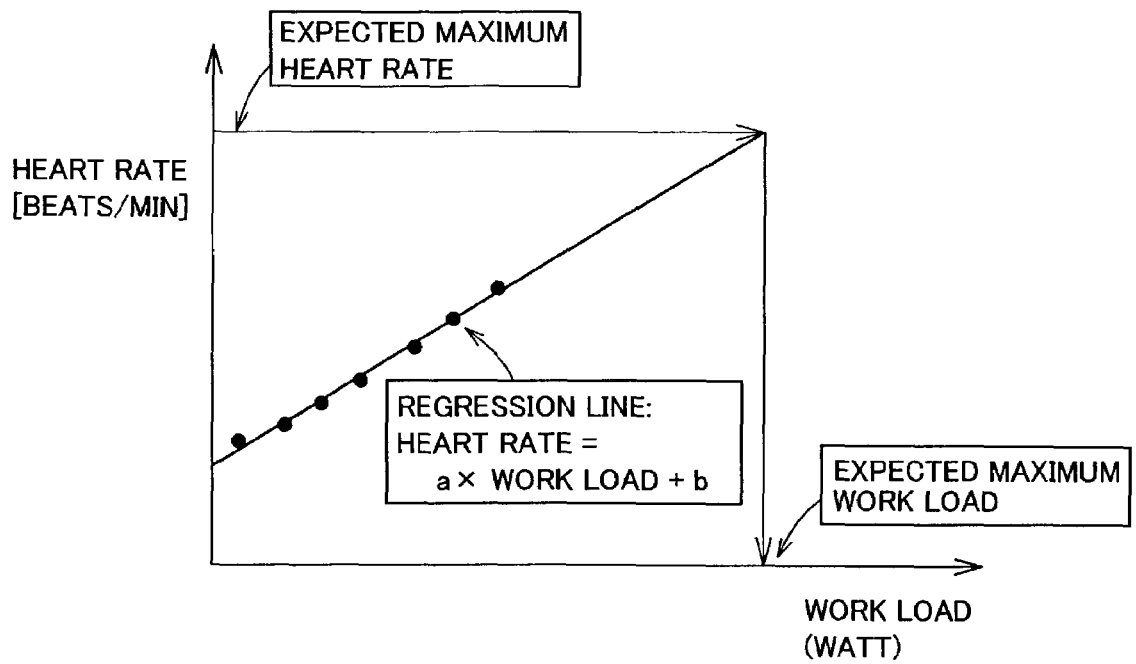
FIG. 16 shows a relation between the work load and the heart rate.

Although the maximum work load at this time is obtained by working out until completely exhausted, it can be obtained from a relation between the work load and the heart rate at the extreme. FIG. 16 shows the relation between the work load and the heart rate. Since the heart rate with respect to the work load is expressed as a regression line: heart rate=a×work load+b as shown in FIG. 16, once the maximum heart rate is obtained, the maximum work load can be obtained from the relevant value. The maximum heart rate can be obtained as (220−age).

Further, taking advantage of the report that the AT work load on average appears at the maximum work load of about 50% [from the publication: "Exercise Physiology in Health and Disease", Wasserman K. and Whipp B. J.], the fat burning rate with the work load greater than the AT work load can be obtained from the following expression (7).

$$\text{Fat burning rate}(>AT)\,[\%] = -0.5 \times (\text{work load during exercise}/\text{AT work load} \times 100) + 100 \quad (7)$$

Based on the fat burning rate calculated from the above expression and the consumed calories, the fat burning amount per unit time is calculated using the expression (5) above (ST45).

Further, from the exercise time, the consumed calories per unit time and the fat burning amount per unit time, accumulated values of the consumed calories and the fat burning amount are calculated (ST46), and these values are displayed on the display unit of display 8 as described above (ST47).

When the training end key on key input device 7 in FIG. 1 is depressed (ST48), "end training" is displayed on display 8 (ST49), and the program is terminated (ST50). When the training end key is not depressed, the exercise program is continued, and the process steps ST42-ST48 are repeated.

In the above-described embodiment, the fat burning rate has been calculated with the AT work load determined in accordance with the pattern in variation of the power of heart rate variability under the work load. However, instead of the power of heart rate variability, entropy of the heartbeat rate variability may be employed.

Here, to obtain the entropy of the heart rate variability, Power (n) of the heart rate variability is measured to obtain 128 pieces of data, or at intervals of every two minutes, and frequency distribution in percentage is calculated therefrom. From P(i)=f(i)/f, and according to the following expression (8), the entropy of the heart rate variability is calculated.

Entropy of heart rate variability:

$$H = -\Sigma P(i) \log_2 P(i) \qquad (8)$$

FIGS. 9A and 9B illustrate a relation between the entropy of the heart rate variability and the work load with the lapse of time. As shown in FIGS. 9A and 9B, as the work load increases at a constant ratio, the entropy of the heart rate variability attains the minimum value at a certain time point. This time point is designated as an AT point, and the work load at this time point is designated as the AT work load.

Alternatively, the AT work load can be determined from the anaerobic threshold (AT) that is obtained by breathing gas analysis from an inflection point of an increase of carbon dioxide emission ($VCO_2$) with respect to an increase of oxygen intake ($VO_2$) and an ascending point of ventilation equivalent ($VE/VO_2$) with respect to $VO_2$, or it can be determined from an inflection point of double product that is the product of the heart rate and the blood pressure under vasoconstriction.

The double product represents a degree of burden on cardiac muscles, which is described in detail, e.g., in "Accommodation of Body Function" (edited by Haruo Ikegami, Asakura Shoten, Mar. 15, 1997).

Still further, the anaerobic threshold (AT) may be obtained from a change of heart rate variation spectrum power value. This heart rate variation spectrum power value is obtained as power spectrum (a curve representing a relation between frequency and energy) that is obtained by Fast Fourier Transform (FFT) from the frequency and its strength (power) of a frequency component included in the heart rate variation.

Although display 8 described above displays consumed calories, fat burning amount and their accumulated values as shown in FIG. 12, it may also display a remaining time. Specifically, a sought-after fat burning amount input via key input device 7 in advance, a fat burning amount consumed by the exercise so far, and the exercise time may be used to calculate the remaining time required to reach the target fat burning amount for display.

In this case, the following expressions are employed:

Remaining fat burning amount(g)=target fat burning amount(g)−accumulated fat amount (g)

Remaining time(min)=remaining fat burning amount (g)÷consumed calories(kcal/min)÷fat burning rate(%)

Figure 18:
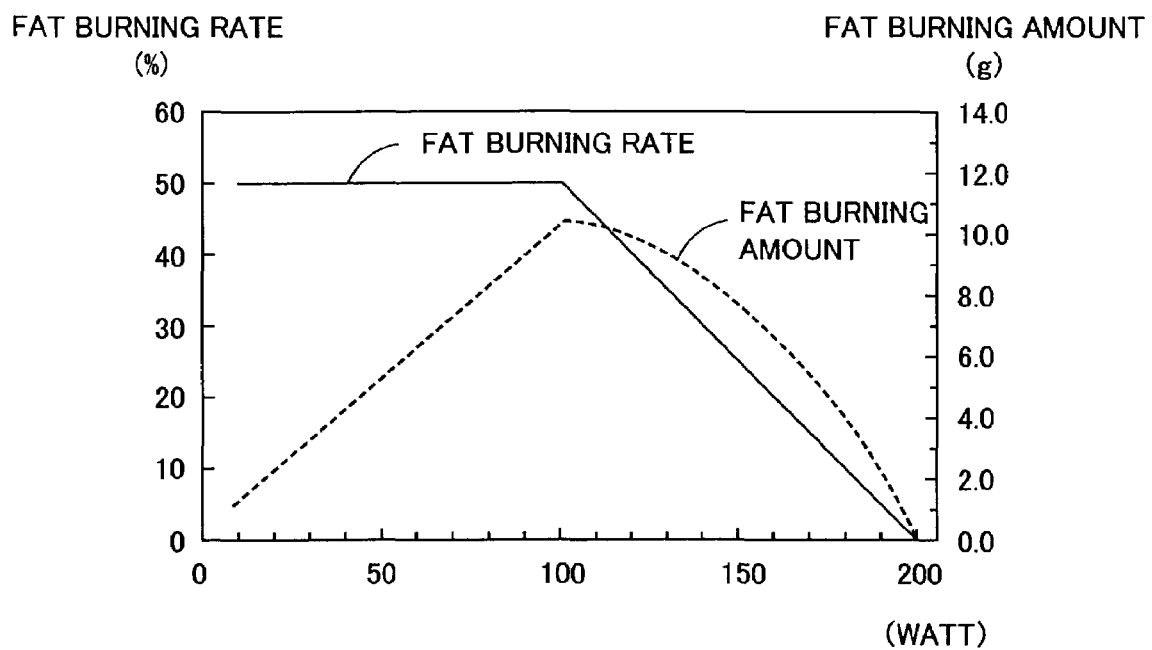
FIG. 18 shows a relation between the fat burning rate and the fat burning amount.

A relation between the fat burning rate and the fat burning amount is now explained. FIG. 18 shows the relation between the fat burning rate and the fat burning amount at the time of exercise for 30 minutes, with the AT level being 100 Watt. As shown in FIG. 18, the fat burning rate is constant until the AT level. The fat burning amount increases as the work load increases, and it reaches a maximum at the AT level. After exceeding the AT level, the fat burning rate and the fat burning amount both decrease. As such, the fat can be burnt most efficiently with the exercise at the AT level.

INDUSTRIAL APPLICABILITY

As described above, according to the fat burning value calculating method, the fat burning value calculating apparatus and the exercise machine of the present invention, a physiological signal varying at times during exercise is detected to calculate a fat burning rate. Thus, compared to the conventional techniques (including the one taking no account of a change of the fat burning rate and the one employing a table prepared such that the fat burning amount is in reverse proportion to the work load), the fat burning rate and the fat burning amount can be calculated more accurately, and accordingly, accurate and valid information can be provided to a person who exercises with an aim to burn the fat.

The invention claimed is:

1. A fat burning value calculating apparatus comprising:
   a physiological signal measuring portion to measure a physiological signal from a living body during exercise,
   an anaerobic threshold determining portion to determine an anaerobic threshold from the physiological signal obtained by the physiological signal measuring portion, and
   a fat burning rate calculating unit to calculate a fat burning rate during the exercise based on exercise intensity at the determined anaerobic threshold.

2. The fat burning value calculating apparatus according to claim 1, wherein said fat burning rate calculating portion calculates the fat burning rate from a ratio between the exercise intensity at the anaerobic threshold and exercise intensity at a time of the exercise.

3. The fat burning value calculating apparatus according to claim 1, wherein said exercise intensity at the anaerobic threshold is determined from a change of a power value of variability of heart rate intervals obtained by the physiological signal.

4. The fat burning value calculating apparatus according to claim 1, wherein said exercise intensity at the anaerobic threshold is determined from a change of entropy of variability of heart rate intervals obtained by the physiological signal.

5. The fat burning value calculating apparatus, according to claim 1, wherein said exercise intensity at the anaerobic threshold is determined from a change of a power value of heart rate variation spectrum.

6. The fat burning value calculating apparatus according to claim 1, wherein said exercise intensity at the anaerobic threshold is determined from a change of a product of a heart rate and a blood pressure under vasoconstriction.

7. A fat burning value calculating apparatus comprising:
   a physiological signal measuring portion to measure a physiological signal from a living body during exercise,
   a determining portion to determine exercise intensity from the physiological signal obtained by the physiological signal measuring portion, and
   a fat burning rate calculating portion to calculate a fat burning rate during the exercise employing said determined exercise intensity and a previously measured anaerobic threshold.

8. The fat burning value calculating apparatus according to claim 1, further comprising a fat burning amount calculating portion to calculate a fat burning amount from the fat burning rate calculated by said fat burning rate calculating portion and consumed calories calculated from exercise intensity.

9. The fat burning value calculating apparatus according to claim 8, further comprising:
   an input portion to input a fat burning amount as a target, and
   a remaining time calculating portion to calculate a remaining time required to reach the target fat burning amount from the fat burning amount calculated by said fat burning amount calculating portion and an exercise time.

10. The fat burning value calculating apparatus according to claim 8, further comprising an accumulated value calculating portion to calculate an accumulated value of the fat burning amount from the start of the exercise.

11. The fat burning value calculating apparatus according to claim 2, wherein said exercise intensity at the anaerobic threshold is determined from a change of a power value of variability of heart rate intervals obtained by the physiological signal.

12. The fat burning value calculating apparatus according to claim 2, wherein said exercise intensity at the anaerobic threshold is determined from a change of entropy of variability of heart rate intervals obtained by the physiological signal.

13. The fat burning value calculating apparatus according to claim 2, wherein said exercise intensity at the anaerobic threshold is determined from a change of a power value of heart rate variation spectrum.

14. The fat burning value calculating apparatus according to claim 2, wherein said exercise intensity at the anaerobic threshold is determined from a change of a product of a heart rate and a blood pressure under vasoconstriction.

* * * * *

UNITED STATES PATENT AND TRADEMARK OFFICE
CERTIFICATE OF CORRECTION

| | | |
|---|---|---|
| PATENT NO. | : 7,326,150 B2 | Page 1 of 1 |
| APPLICATION NO. | : 10/181043 | |
| DATED | : February 5, 2008 | |
| INVENTOR(S) | : Yoshitake Oshima et al. | |

It is certified that error appears in the above-identified patent and that said Letters Patent is hereby corrected as shown below:

On the Title page, under (73) Assignee:

Delete "Tokyo" and replace with -- Kyoto --.

Signed and Sealed this

Twenty-fourth Day of June, 2008

JON W. DUDAS
*Director of the United States Patent and Trademark Office*